United States Patent
Muisener et al.

(12) 
(10) Patent No.: US 6,739,719 B2
(45) Date of Patent: May 25, 2004

(54) LENS BLANK CONVENIENT FOR MASKING UNPLEASANT ODOR AND/OR DELIVERING A PLEASANT ODOR UPON EDGING AND/OR SURFACING, AND PERFUME DELIVERING LENS

(75) Inventors: Richard Muisener, Tarpon Springs, FL (US); Herbert Mosse, Lutz, FL (US); Sidney S. White, North Seminole, FL (US)

(73) Assignee: Essilor International Compagnie Generale d'Optique, Charenton Cedex (FR)

( * ) Notice: Subject to any disclaimer, the term of this patent is extended or adjusted under 35 U.S.C. 154(b) by 0 days.

(21) Appl. No.: 10/170,990

(22) Filed: Jun. 13, 2002

(65) Prior Publication Data

US 2003/0231280 A1 Dec. 18, 2003

(51) Int. Cl.$^7$ ................................................. G02C 7/02
(52) U.S. Cl. ........................... 351/159; 351/177; 451/43
(58) Field of Search ............................. 451/43; 351/159, 351/177

(56) References Cited

U.S. PATENT DOCUMENTS

| | | | |
|---|---|---|---|
| 4,631,072 A | * 12/1986 | Koller | ........................... 51/309 |
| 5,658,184 A | * 8/1997 | Hoopman et al. | ............ 451/28 |

FOREIGN PATENT DOCUMENTS

| | | | | |
|---|---|---|---|---|
| DE | 3321933 | 12/1994 | | |
| JP | 61147201 | 4/1986 | | |
| JP | 2174847 | 6/1990 | | |
| JP | 2223909 | 6/1990 | | |
| JP | 04068036 A | * 3/1992 | ............ | C08J/7/02 |
| JP | 04294301 A | * 10/1992 | ............ | G02B/1/04 |
| WO | WO 02/08820 | 1/2002 | | |
| WO | WO 02/27539 | 4/2002 | | |

* cited by examiner

*Primary Examiner*—Scott J. Sugarman
(74) *Attorney, Agent, or Firm*—Fulbright & Jaworski L.L.P.

(57) ABSTRACT

The present invention relates to the field of reducing or eliminating unpleasant odor and/or delivering a pleasant odor upon edging and/or surfacing lenses, and more particularly ophthalmic lenses. The present invention also relates to perfume delivering ophthalmic lenses, that deliver a slight perfume pleasant for the wearer of eyeglasses.

40 Claims, 1 Drawing Sheet

LENS BLANK CONVENIENT FOR MASKING UNPLEASANT ODOR AND/OR DELIVERING A PLEASANT ODOR UPON EDGING AND/OR SURFACING, AND PERFUME DELIVERING LENS

BACKGROUND OF THE INVENTION

1. Field of the Invention

The present invention relates to the field of reducing or eliminating unpleasant odor and/or delivering a pleasant odor upon edging and/or surfacing lenses, and more particularly ophthalmic lenses.

The present invention also relates to perfume delivering ophthalmic lenses, that deliver a slight perfume pleasant for the wearer of eyeglasses.

2. Description of Related Art

In the present application, it is meant under the term "lens" any organic or mineral glass substrate, either treated or not, for use in eyewear or in optical devices, and more particularly an ophthalmic lens.

An ophthalmic lens result from a series of molding and/or surfacing/polishing operations determining the geometry of both convex and concave optical surfaces of said lens, followed by appropriate surface treatments.

The last finishing step of an ophthalmic glass is an edging step consisting in machining the peripheral edge (or periphery) of the lens so as to conform it to the required dimensions for adapting the lens to the lens frame in which it is intended to be accommodated. Edging is generally carried out on a grinding machine comprising diamond abrasive wheels that perform the machining step as defined hereabove.

Some lenses, in particular lenses comprising sulphur derived products such as polythiourethans or polyepisulfides, generally generate unpleasant odor during this edging step, and also during the previous surfacing step.

One of the objects of the invention aims at offering a means allowing to perform an edging and/or a surfacing step without generating any unpleasant odor.

It has already been previously suggested to introduce fragrances (anti-odor or perfume agents) in the mould body of the lens, before curing the lens. This is the case, for example, in the Japanese patent JP 61147201 relating to a method for reducing or eliminating unpleasant odor generated in the stage of cutting or grinding of a plastic lens by incorporating from 0.005 to 1.0 wt. % of at least one hydrocarbon or heterocyclic fragrance imparting compound.

However, higher amounts of fragrance imparting compound lead to a decrease of the mechanical properties of the lens, and too strong shedding of the fragrance may also occur. Besides, most of the fragrance contained in the body of the lens has no real activity for the sought purpose, because the active part of the perfume is only situated in the part of the lens to be ground (i.e. near the surface).

Some documents of the prior art, specifically mentioning a method for reducing or deodorizing the offensive smell generated during the edging step of a plastic lens, describe the incorporation of fragrances in the cooling water which comes into contact with the lens when the lens is edged. In particular, the Japanese patent JP 2174847 discloses the incorporation in the cooling water of 0.001 to 0.01% weight of at least one hydrocarbon or heterocyclic fragrance compound with respect to the weight of the cooling water.

However, this technique is very expensive because high amounts of fragrance have to be used.

The object of the present invention is therefore a means which remedies theses disadvantages.

In particular, the object of the invention is a lens blank prepared by coating the edge of said lens blank with a fragrance containing coating, convenient for masking unpleasant odor and/or delivering a pleasant odor upon edging and/or surfacing.

By lens blank is meant in the sense of the application a lens that needs to be subjected to a subsequent step of surfacing or edging.

A lens blank can consequently encompass:
- a lens that has been molded or surfaced on both sides (that has its two optical surfaces at the required geometry), and needs only to be edged, that case being the preferred case;
- a lens that needs to be surfaced on one side, generally the back side (close to the eye of the wearer).

The application of a coating onto the peripheral edge of a lens is known in the prior art.

Thus, the international patent application WO 02/08820 specifically describes the appliance of a colored coating onto the edge of an optical lens, for enhancing the cosmetic appearance of eyeglasses by reducing the appearance of the white ring appearing along the perimeter of the face of the lens when viewing eyeglasses from the front, and by reducing the appearance of the white film in the edge of the lens when viewing eyeglasses from the side. This optical lens may also prevent or reduce the glare from light entering through the edge.

In the case of thick spectacle lenses, in which the mount holding the spectacle lenses only partially embraces the respective spectacle lens rim, the German patent DE 3321933 proposes to apply an opaque coating on the regions of the edge not covered by the mount in order to solve the latter technical problem.

The international patent application WO 02/27539 relates to a method of coating the peripheral edge of a lens, the coating eliminating the need for an edge polishing step in the manufacture of lenses. The coating also prevents the ingression of moisture, and protects the edge against chemical attack, such as from solvents or grease. This method of coating further provides an ability to apply a colored coating on the edge of the lens, such that a fashionable range of lenses may be provided for use in rimless spectacle frames, for instance.

Finally, the Japanese patent JP 2223909 describes a lens for eye spectacles prepared by coating the lens with three layers of films effective in controlling unpleasant odors from the air: a $SiO_2$ film produced by physical vapor deposition (PVD), a color film containing nitrides, carbides or oxides, and a $TiO_2$ film also produced by PVD. There is no mention in this patent of an application of these coatings on the peripheral edge of a lens.

Consequently, none of the above-cited previous documents appear to describe or suggest to apply a fragrance containing coating on the edge of the lens.

SUMMARY OF THE INVENTION

The present invention provides a lens blank having front and back optical surfaces and a peripheral edge, wherein the peripheral edge is coated with a fragrance containing temporary coating.

By temporary coating is meant in the sense of the application a coating that is partially or completely eliminated during edging and/or surfacing, afterwards.

By fragrance containing temporary coating is meant in the sense of the application a temporary coating that delivers a noticeable pleasant odor and/or masks unpleasant odors upon edging and/or surfacing. Thus, unpleasant odors that could appear during edging and/or surfacing are either reduced or eliminated. The temporary nature of the coating ensures that the user does not experience an odor emanating from his lenses.

Also meant as fragrance containing temporary coatings are temporary coatings including materials that are able to neutralize unpleasant odors rather than masking them and/or including agent(s) capable of eliminating one's ability to smell unpleasant odors.

Advantageously, the fragrance temporary coating is opaque, and barely noticeable on the peripheral edge of the lens blank.

Preferably, the fragrance containing temporary coating comprises fragrance containing microcapsules, that do not release the fragrance, even during storage, until a mechanical action (edging the lens blank or surfacing the optical surface) is applied to the capsules, these microcapsules being embedded in a polymer matrix in order to promote the durability of the coating during any handling of the lens prior to processing, for instance prior to edging and/or surfacing.

By microcapsule is meant in the sense of the application an outer continuous self-supporting wall surrounding an inner fill material, which may be visualized as a hollow or liquid-core sphere in which up to 80% of the total volume is a volatile material protected by an impermeable solid shell. Ordinarily, microcapsules are more or less spherically or spheroidally shaped discrete bodies, showing a micronic diameter ranging from 1 to 2000 microns (0.001 to 2 mm), and more frequently within the range of about 1 to 500 microns (0.001 to 0.5 mm).

By fragrance containing microcapsule is meant in the sense of the application a polymeric or inorganic shell, encapsulating at least one fragrance, preferably at least one oleophilic volatile fragrance.

In the present application, microcapsules are advantageously polymeric shells encapsulating at least one oleophilic volatile fragrance.

Since the polymeric shell is a good barrier layer, the volatile fragrance can be stored in the shell for long periods of time (months for instance) with only a faint odor. Thus, the protected volatile fragrance is only released, when desired upon breaking the outer shell through simple shear, for instance as the mechanical edging and/or surfacing of the lens blank shears the microcapsules storing the fragrance.

When surfacing an optical surface of the lens blank, the edge coating is partially machined at the same time by the surfacing tool so that fragrances are released.

The polymeric shells are preferably urea-formaldehyde shells, silica shells or polyoxymethylene-urea shells.

Upon fragrance containing microcapsules comprising urea-formaldehyde shells, mention may be made of commercial urea-formaldehyde capsules encapsulating fragrances such as pure essential oils of Aura Cacia, lemongrass, eucalyptus and bergamot, or International Fragrance and technology mint #195621, mulberry #195622, and orange #195621.

The fragrance containing microcapsules comprising silica shells, preferably encapsulates fragrances such as a pure essential oil selected from the pure essentials oils of Aura Cacia, lemongrass, eucalyptus, bergamot, cinnamon leaf, and their mixtures.

Upon fragrance containing microcapsules comprising polyoxymethylene urea polymer shells, mention may be made of the Powder Bouquet® fragrance microcapsules powder sold by the 3M Company, or fragrance being selected from a list of over 70 fruit, food and floral scents provided by the Celessance Company.

The fragrance containing microcapsules of the invention are embedded in a polymer matrix. The polymer matrix preferably comprises a water-soluble polymer, and in particular a polyvinyl alcohol or a polyester polymer.

The present invention also provides a method of masking unpleasant odors and/or delivering a pleasant odor upon edging and/or surfacing a lens, including the steps of:

a) providing a lens blank having front and back optical surfaces and a peripheral edge, b) applying a fragrance containing coating composition to said peripheral edge, c) drying said fragrance temporary coating composition to a form fragrance temporary coating on said peripheral edge, and thus obtaining an edge-coated lens blank, d) edging and/or surfacing said edge-coated lens blank to a required geometry, said edge-coated lens blank delivering the fragrance that is contained in the fragrance temporary coating composition, and e) optionally removing any excess of fragrance temporary coating remaining on said edge-coated lens blank, and thus obtaining an edged and/or surfaced lens.

The fragrance containing coating composition of the invention is preferably in the form of an aqueous suspension, comprising the fragrance containing microcapsules of the invention, as described above, and at least one water-soluble polymer as a binder.

The water-soluble polymer is preferably a polyvinyl alcohol or a polyester polymer.

The fragrance containing coating composition can be applied on the peripheral edge of a lens blank by any convenient means, for example by brushing or roll coating the edge of the lens.

In an other embodiment of the invention, the fragrance containing coating is made permanent, i.e. is deposited on the edge of an already edged lens. Such a permanent fragrance containing coating is then designed to deliver a pleasant odor to the wearer of eyeglasses.

Thus, the present invention also provides a perfume-delivering lens having front and back optical surfaces and a peripheral edge already edged to a required geometry, wherein said peripheral edge is coated with a fragrance containing permanent coating.

By perfume delivering lens is meant in the sense of application a lens that has already been edged and delivers a permanent slight perfume pleasant for the wearer of the eyeglasses.

The fragrance containing permanent coating of the invention has the same characteristics as the fragrance containing temporary coating of the invention, i.e. a fragrance containing coating comprising fragrance containing microcapsules embedded in a polymer matrix, as described above.

Any shear of the coated edge that can occur during handling of the spectacles will deliver the perfume.

The perfume-delivering lens of the invention can be prepared by the following method:

a) providing a lens whose peripheral edge has been edged to a required geometry, b) applying a fragrance containing coating composition to said peripheral edge, c) drying said fragrance containing coating composition to form a fragrance permanent coating on said peripheral edge, and thus obtaining a lens delivering the fragrance that is contained in the fragrance durable coating.

The same fragrance containing coating composition as previously disclosed can be used to make the perfume delivering lenses according to the invention.

This fragrance containing coating composition can be applied in the same manner as previously disclosed for the fragrance containing temporary coatings.

The fragrance containing temporary coating or the fragrance containing permanent coatings can be applied on any organic or mineral glass substrates material for use in eyewear or in optical devices especially ophthalmic lenses.

The organic material can be a polyallylic material such as obtained from CR39®, a poly[diethoxybisphenolA] dimethacrylate], a thermoplastic polycarbonate (PC), a polythiourethan, a polyepisulfide.

The invention has several advantages:
1) Long ability to deliver a perfume because the encapsulation stabilizes the perfume,
2) the release of perfume is maximal during the edging and/or surfacing stage.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE ILLUSTRATIVE EMBODIMENTS

Figure 1:
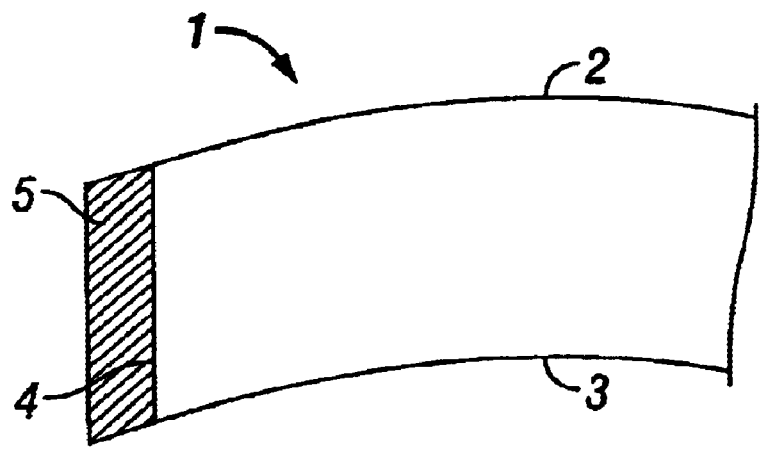
FIG. 1 A cross-sectional schematic view of a lens blank according to one aspect of the present invention. The lens blank 1 can have a front optical surface 2, a back optical surface 3, and a peripheral edge 4. The peripheral edge 4 can be coated with a fragrance containing temporary coating 5.
Figure 2:
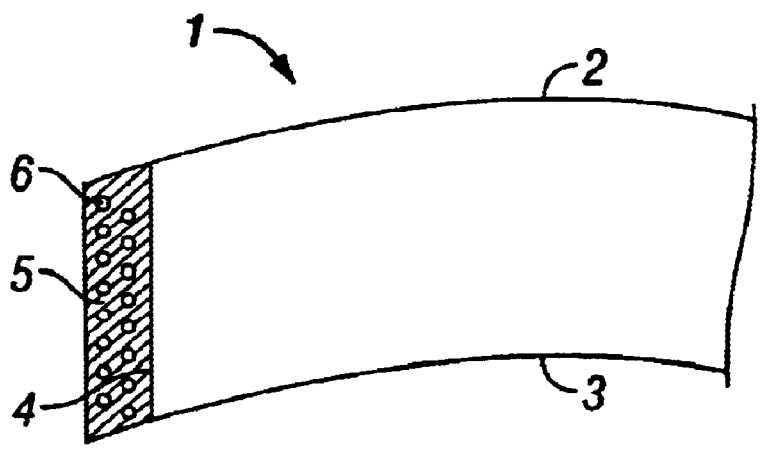
FIG. 2 A cross-sectional schematic view of a lens blank according to one aspect of the present invention. The fragrance containing temporary coating 5 can comprise fragrance containing microcapsules 6.

The following examples illustrate the invention without in any way limiting its scope.

EXAMPLES

I. Preparation of Fragrance Containing Microcapsules

I.1. Preparation of Fragrance Containing Urea-Formaldehyde Microcapsules: Following U.S. Pat. No. 3,516,941, Example 1.

Day 1:

24 g urea (Adrich ACS Reagent 99%) was dissolved in 48 g Aqueous Formaldehyde (Aldrich 37% soluble in water) during approximately 20 min. Then, approximately 10 drops of triethanolamine (Aldrich) were added to achieve pH8. The solution was then heated to 70° C. for one hour before adding 100 g of deionized water.

Day Two:

43.25 g of the above solution was removed and the pH was adjusted to 5 with citric acid (Aldrich 10% solution). 14 g of at least one Fragrance, selected from the pure essential oils of Aura Cacia, lemongrass, lavender, eucalyptus, bergamot and International Fragrance and Technology mint #195624, mulberry #195622, and orange #195621, was added. After adjusting the solution's pH to 3.5 and heating to 40 to 45° C. for 40 min, 15 g of deionized water was added. The solution was then heated for 3 hrs. 55 g chilled deionized water was then added. The solution was stirred during the entire process.

Purification

The solution was centrifuged at 5000 rpm for 10 minutes to separate microcapsules from water and non-encapsulated species. The capsules were washed with DI water and centrifuged again.

I.2. Preparation of Fragrance Containing Silica Microcapsules: Following U.S. Pat. No. 6,238,650 Example 1.

10 g of a pure essential oil (selected from the pure essentials oils of Aura Cacia, lemongrass, lavender, eucalyptus, bergamot, and cinnamon leaf) were added to a mixture comprising 10 g of tetraethoxysilane (TEOS), 40 g of deionized water and 4 g of cetyltrimethylammonium bromide. This solution was mixed in a high shear mixer in cooling bath at 0.5° C. for 1 hour. 58 g of 11.3 pH NaOH was added. The solution was stirred at room temperature for 24 hours. The solution was then centrifuged at 5000 rpm for 10 minutes to separate microcapsules, washed with deionized water and centrifuged again.

II. Preparation of Edge Coating Compositions

The fragrance containing compositions C1 to C11 according to the invention comprise either the commercial fragrance containing microcapsules marketed under the name 3M POWER BOUQUET™ 9850 by the 3M company or the fragrance containing microcapsules as synthesized above. The compositions C1 to C11 were prepared by mixing the ingredients listed in table 1 below as follows:

for each composition C1 to C10, the ingredients are simply added and mixed until an even consistency is obtained;

for composition C11, 1 g of Celessance International KT82QS available from CELESSANCE Company was slowly mixed into 2 g of deionized water; this mixture was then added to 1 g of an aqueous solution of a water-soluble polyester resin marketed under the name AQ55 solution by the Eastman Chemical Company, and mixed until an even consistency was achieved.

TABLE 1

| Composition | Ingredients | WEIGHT (g) |
|---|---|---|
| C1 | 10% POLY VINYL ALCOHOL | 5.0 |
|  | LAVENDER TEOS BASED CAPSULES | 5.0 |
| C2 | ORANGE FORMALDEHYDE-UREA-CAPSULES | 1.8 |
|  | AQ55 IN DI 34% SOLIDS | 2.0 |
| C3 | 3 M POWDER BOUQUET 9850 ™ | 1.0 |
|  | AQ55 IN DI 34% SOLIDS | 4.0 |
| C4 | 20% POLY VINYL ALCOHOL | 4.0 |
|  | 3 M POWDER BOUQUET ™ 9850 | 1.0 |
|  | DI water | 2.0 |
| C5 | 20% POLY VINYL ALCOHOL | 4.0 |
|  | MINT FORMALDEHYDE-UREA | 4.0 |
| C6 | 20% POLY VINYL ALCOHOL | 4.0 |
|  | ORANGE FORMALDEHYDE-UREA CAPSULES | 4.0 |
| C7 | 20% POLY VINYL ALCOHOL | 4.0 |
|  | DI water | 2.0 |
|  | 3 M POWDER BOUQUET ™ 9850 | 1.0 |
| C8 | 20% POLY VINYL ALCOHOL | 4.0 |
|  | MINT FORMALDEHYDE-UREA CAPSULES | 4.0 |
|  | FC430 ™ (3 M surfactant) | 0.005 |
| C9 | AQ55 IN DI 34% SOLIDS | 4.0 |
|  | 3 M POWDER BOUQUET ™ 9850 | 1.0 |
| C10 | AQ55 IN DI 34% SOLIDS | 4.0 |
|  | MINT FORMALDEHYDE-UREA CAPSULES | 4.0 |

TABLE 1-continued

| Composition | Ingredients | WEIGHT (g) |
|---|---|---|
| C11 | AQ55 IN DI 34% SOLIDS | 1.0 |
| | DI water | 2.0 |
| | CELESSANCE INTERNATIONAL KT82QS ™ | 1.0 |

DI water: deionized water
AQ-55: a water-soluble polyester resin from Eastman Chemical
AQ-55 in DI 34% solids: a deionized water solution containing 34% by weight of the water soluble polyester AQ-55.
3 M POWDER BOUQUET ™ 9850: commercial fragrance containing microcapsules.
CELESSANCE INTERNATIONAL KT82QS ™: from CELESSANCE Company III. Preparation of Edge Coated Lenses and Edging of Corresponding Lenses Each of the prepared coating compositions were applied on the peripheral edge of either a lens that has already been edged to the required geometry or a lens blank that still needs to be edged.

Concerning the coating of a finished lens, it has been observed that:
upon drying the coating composition onto the edge of the lens, there were no changes in the appearance of the lens except a slightly more opaque edge, and
the coated finished lens contained a slight odor that dissipated greatly after a few days.

Lenses coated with the edge compositions $C_2$ to $C_8$, $C_{10}$, $C_{11}$ were manually rubbed on their edge with a finger nail (to and for movement) to simulate handling of spectacles.

Each time the edges were rubbed, a pleasant odor was released.

Concerning the coating of a blank lens, it has been observed that:
a week after coating the peripheral edge of several blanks lenses with the composition C9, nine lenses were edged utilizing dry conditions. After edging the first lens, an odor was present in the machine. Soon, after edging a few lenses, the entire room had a pleasant odor as noted by several other witnesses in the room.
lenses coated with edge composition n°1 delivered odors but their edge was sensitive to scratching (became hazy upon scratching).

What is claimed is:

1. A lens blank having front and back optical surfaces and a peripheral edge, wherein the peripheral edge comprises a fragrance containing temporary coating.

2. The lens blank of claim 1, wherein the fragrance containing temporary coating comprises fragrance containing microcapsules embedded in a polymer matrix.

3. The lens blank of claim 2, wherein the fragrance containing microcapsules comprise a polymeric shell encapsulating at least one oleophilic volatile fragrance.

4. The lens blank of claim 3, wherein the shell is an urea-formaldehyde shell.

5. The lens blank of claim 3, wherein the shell is a silica shell.

6. The lens blank of claim 3, wherein the shell is polyoxymethylene-urea polymer shell.

7. The lens blank of claim 4, wherein the oleophilic volatile fragrance is selected from the pure essential oils of Aura Cacia, lemongrass, eucalyptus and bergamot, the International Fragrance and Technology mint #195624, mulberry #195622, and orange #195621, and their mixtures.

8. The lens blank of claim 5, wherein the oleophilic volatile fragrance is selected from the pure essential oils of Aura Cacia, lemongrass, eucalyptus, bergamot, cinnamon leaf and their mixtures.

9. The lens blank of claim 6, wherein the fragrance is selected from fruit, food, and floral scents and their mixtures.

10. The lens blank of claim 2, wherein the polymer matrix comprises a water-soluble polymer, and preferably a polyvinyl alcohol or a polyester polymer.

11. A perfume delivering lens having front and back optical surfaces and a peripheral edge already edged to a required geometry, wherein the peripheral comprises a fragrance containing permanent coating.

12. The perfume delivering lens of claim 11, wherein the fragrance containing permanent coating comprises fragrance containing microcapsules embedded in a polymer matrix.

13. The perfume delivering lens of claim 12, wherein the fragrance containing microcapsules comprise a shell encapsulating at least one oleophilic volatile fragrance.

14. The perfume delivering lens of claim 13, wherein the shell is an urea-formaldehyde shell.

15. The perfume delivering lens of claim 13, wherein the shell is a silica shell.

16. The perfume delivering lens of claim 13, wherein the shell is a polyoxymethylene-urea polymer shell.

17. The perfume delivering lens of claim 14, wherein the oleophilic volatile fragrance is selected from the pure essential oils of Aura Cacia, lemongrass, eucalyptus and bergamot, the International Fragrance and Technology mint #195624, mulberry #195622, and orange #195621, and their mixtures.

18. The perfume delivering lens of claim 15, wherein the oleophilic volatile fragrance is a pure essential oil selected from the pure essential oils of Aura Cacia, lemongrass, eucalyptus, bergamot, cinnamon leaf and their mixtures.

19. The perfume delivering lens of claim 16, wherein the fragrance is selected from fruit, food, and floral scents and their mixtures.

20. The perfume delivering lens of claim 12, wherein the polymer matrix comprises a water-soluble polymer, and preferably a polyvinyl alcohol or a polyester polymer.

21. A method of masking unpleasant odors and/or delivering a pleasant odor upon edging and/or surfacing a lens, comprising:
a) providing a lens blank having front and back optical surfaces and a peripheral edge;
b) applying a fragrance containing coating composition to said peripheral edge;
c) drying said fragrance temporary coating composition to a form fragrance temporary coating on said peripheral edge, and thus obtaining an edged-coated lens blank;
d) edging and/or surfacing said edge-coated lens blank to a required geometry, said edge-coated lens blank delivering the fragrance that is contained in the fragrance temporary coating composition; and
e) removing any excess of fragrance temporary coating remaining on said edge-coated lens blank, and thus obtaining an edged and/or surfaced lens.

22. The method of claim 21, wherein the fragrance containing composition is in the form of an aqueous suspension, comprising fragrance containing microcapsules and at least one water-soluble polymer as a binder.

23. The method of claim 22, wherein the fragrance containing microcapsules comprise a shell encapsulating at least one oleophilic volatile fragrance.

24. The method of claim 23, wherein the shell is an ureaformaldehyde shell.

25. The method of claim 23, wherein the shell is a silica shell.

26. The method of claim 23, wherein the shell is a polyoxymethylene-urea polymer shell.

27. The method of claim 24, wherein the oleophilic volatile fragrance is selected from the pure essential oils of Aura Cacia, lemongrass, eucalyptus and bergamot, International Fragrance and Technology mint #195624, mulberry #195622, and orange #195621 and their mixtures.

28. The method of claim 25, wherein the oleophilic volatile fragrance is selected from the pure essential oils of Aura Cacia, lemongrass, eucalyptus, bergamot, cinnamon leaf and their mixtures.

29. The method of claim 26, wherein the fragrance is selected from fruit, food, and floral scents and their mixtures.

30. The method of claim 22, wherein the water-soluble polymer is a polyvinyl alcohol or a polyester polymer.

31. A method of preparing a perfume delivering lens having front and back optical surfaces and a peripheral edge, comprising:
 a) providing a lens whose peripheral edge has already been edged to a required geometry;
 b) applying a fragrance containing coating composition to said peripheral edge; and
 c) drying said fragrance containing coating composition to form a fragrance permanent coating on said peripheral edge, and thus obtaining a lens delivering the fragrance that is contained in the fragrance durable coating.

32. The method of claim 31, wherein the fragrance containing composition is in the form of an aqueous suspension comprising fragrance containing microcapsules and at least one water-soluble polymer as a binder.

33. The method of claim 32, wherein the fragrance containing microcapsules comprise a shell encapsulating at least one oleophilic volatile fragrance.

34. The method of claim 33, wherein the shell is an urea-formaldehyde shell.

35. The method of claim 33, wherein the shell is a silica shell.

36. The method of claim 33, wherein the shell is a polyoxymethylene-urea polymer shell.

37. The method of claim 34, wherein the oleophilic volatile fragrance is selected from the pure essential oils of Aura Cacia, lemongrass, eucalyptus and bergamot, International Fragrance and Technology mint #195624, mulberry #195622, and orange #195621 and their mixtures.

38. The method of claim 35, wherein the oleophilic volatile fragrance is selected from the pure essential oils of Aura Cacia, lemongrass, eucalyptus, bergamot, cinnamon leaf and their mixtures.

39. The method of claim 35, wherein the fragrance is selected from fruit, food, and floral scents and their mixtures.

40. The method of claim 32, wherein the water-soluble polymer is a polyvinyl alcohol or a polyester polymer.

* * * * *